US005620806A

United States Patent [19]
Nakamura et al.

[11] Patent Number: 5,620,806
[45] Date of Patent: Apr. 15, 1997

[54] ORGANIC MATERIAL FOR EL DEVICE AND EL DEVICE

[75] Inventors: Norikazu Nakamura; Shinichi Wakabayashi, both of Nagano, Japan

[73] Assignee: Shinko Electric Industries Co., Ltd., Nagano, Japan

[21] Appl. No.: 337,221

[22] Filed: Nov. 7, 1994

[30] Foreign Application Priority Data

Nov. 10, 1993 [JP] Japan .................................. 5-280930

[51] Int. Cl.$^6$ ............................................. H05B 33/00
[52] U.S. Cl. ........................ 428/690; 428/917; 313/504; 514/187
[58] Field of Search ..................... 428/690, 917; 313/504; 514/187

[56] References Cited

PUBLICATIONS

Tang et al., "Organic electroluminescent diodes," *Applied Physics Letters*, vol. 51, No. 12, Sep. 21, 1987, pp. 913–915.
Hamada et al., "Organic Electroluminescent Devices with 8–Hydroxyquinoline Derivative–Metal Complexes as an Emitter," *Japanese Journal of Applied Physics*, vol. 32, Part 2, No. 4A, Apr. 1, 1993, pp. L514–L515.
Miki et al., "Effect of the Covalent Bond on the Radiative Properties of the Ligand–Localized $^3\pi\pi^*$ state of Rhodium Complexes with Benzo[h]quinoline," *Journal of Physical Chemistry*, vol. 98, No. 24, Jun. 16, 1994, pp. 6059–6062.

Primary Examiner—Charles Nold
Attorney, Agent, or Firm—Staas & Halsey

[57] ABSTRACT

An organic material for EL devices comprising 10-hydroxy-benzo[h]quinoline zinc complex, as well as an EL device with a luminescent layer including the material.

5 Claims, 2 Drawing Sheets

ORGANIC MATERIAL FOR EL DEVICE AND EL DEVICE

BACKGROUND OF THE INVENTION

1. Field of the Invention

The present invention relates to organic materials for EL (electroluminescent) devices and to EL devices, and more particularly it relates to organic materials for EL devices which exhibit electroluminescence upon the application of a voltage, and to EL devices which employ the above-mentioned organic materials.

2. Description of the Related Art

EL devices employing luminescent materials which exhibit electroluminescence upon the application of a voltage are conventionally used in backlights for displays of OA machines such as word processors and for automobile meters and the like.

Although inorganic compounds have conventionally been used as the luminescent materials for such EL devices, high driving voltages have been required when inorganic compounds for EL devices are caused to emit high-intensity light.

Recently, therefore, research has been conducted in regard to organic compounds for EL devices, which allow lower driving voltages (see, for example, C. W. Tang and S. A. VanSlyke: Appl. Phys. Lett. 51. 913 (1987)).

Thin-film EL devices employing such organic compounds are able to have lower driving voltages in comparison with the conventional inorganic compounds for EL devices.

However, the light emitted by organic compounds for EL devices capable of emitting light at sufficient intensity is usually in the green band (492–577 nm).

Consequently, EL devices employing organic luminescent materials have had an inappropriate color for use in backlights of OA machine displays, etc.

On the other hand, EL devices require multiple colors for their use in displays and the like.

SUMMARY OF THE INVENTION

Here, it is an object of the present invention to provide an organic compound for EL devices which exhibits luminescent colors different from conventional organic compounds for EL devices and which is capable of displaying sufficient intensity, and an EL device employing it.

As a result of study aimed at achieving the above-mentioned object, the present inventors have found that an EL device employing a 10-hydroxybenzo[h]quinoline zinc complex as the luminescent material produces yellow-green to yellow luminescent colors at a high intensity upon the application of a driving voltage, and thus the present invention has been completed.

In other words, the present invention provides an organic material for EL devices comprising 10-hydroxybenzo[h]quinoline zinc complex represented by the following formula (I), as well as an EL device employing this organic material.

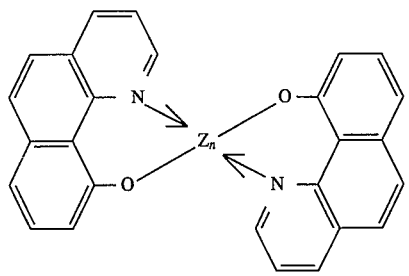

DESCRIPTION OF THE PREFERRED EMBODIMENTS

The organic material of the present invention is used as the material for the luminescent layer of an EL device. That is, the EL device comprises, in order, an anode layer, a hole injection layer, a luminescent layer and a cathode layer, and according to the present invention the material used as the luminescent layer is an organic material which includes the zinc complex represented by the above formula (I). This EL device according to the present invention is capable of emitting high-intensity yellow-green to yellow light when a driving voltage is applied thereto. Furthermore, since the luminescent colors of this EL device are different from those of EL devices using conventional organic materials, the present invention provides more colors for EL devices.

The zinc complex of formula (I) of the present invention may be obtained by, for example, reacting 10-hydroxybenzo[h]quinoline represented by the following formula (II) with zinc acetate.

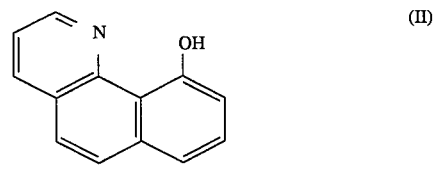

This reaction may be carried out by adding a solution of zinc acetate to a solution of 10-hydroxybenzo[h]quinoline represented by formula (II) dissolved in a solvent such as methanol, stirring the mixture at room temperature for a specified period of time, and then boiling it for a specified period of time.

The reaction product is purified if necessary and then used as the luminescent material for an EL device.

Figure 1:
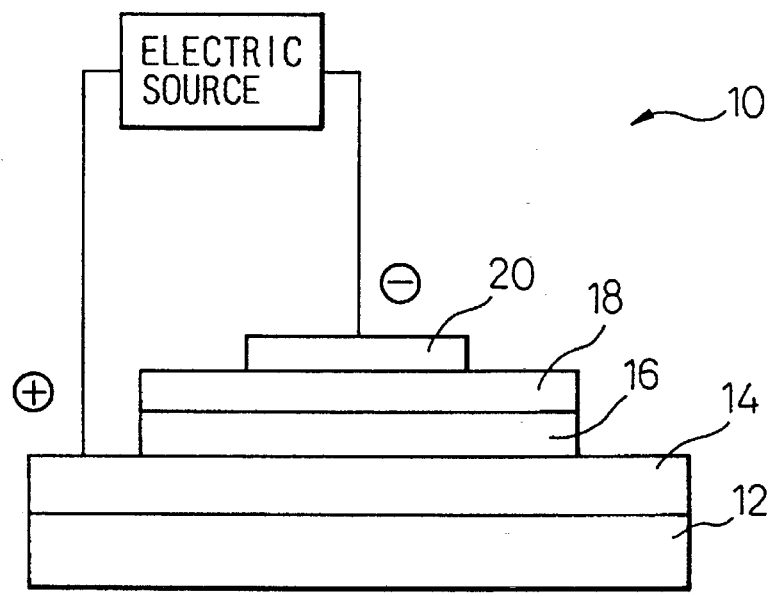
FIG. 1 is a drawing for explanation of an embodiment of an EL device according to the present invention.

The EL device used may have the construction shown, for example, in FIG. 1. The EL device 10 shown in FIG. 1 comprises an ITO transparent electrode (anode) 14 (indium/tin alloy) formed on a transparent glass plate 12, on which are formed in order a hole injection layer 16 composed of a tetraphenyldiamine derivative, a luminescent layer 18 composed of the 10-hydroxybenzo[h]quinoline zinc complex represented by formula (I), and an upper electrode (cathode) 20 composed of a metal such as aluminum.

The hole injection layer 16, luminescent layer 18 and upper electrode 20 may be formed by vacuum deposition. Especially, the hole injection layer 16 and the luminescent layer 18 may be formed by continuous deposition in a high vacuum of about $10^{-6}$ Torr without interrupting the vacuum state.

The anode of this EL device 10 is the ITO transparent electrode 14 and the cathode is the upper electrode 20, and upon the application of a direct current or pulse voltage from a electric source, the luminescent material of the luminescent layer 18 is excited and emits light.

Figure 2:
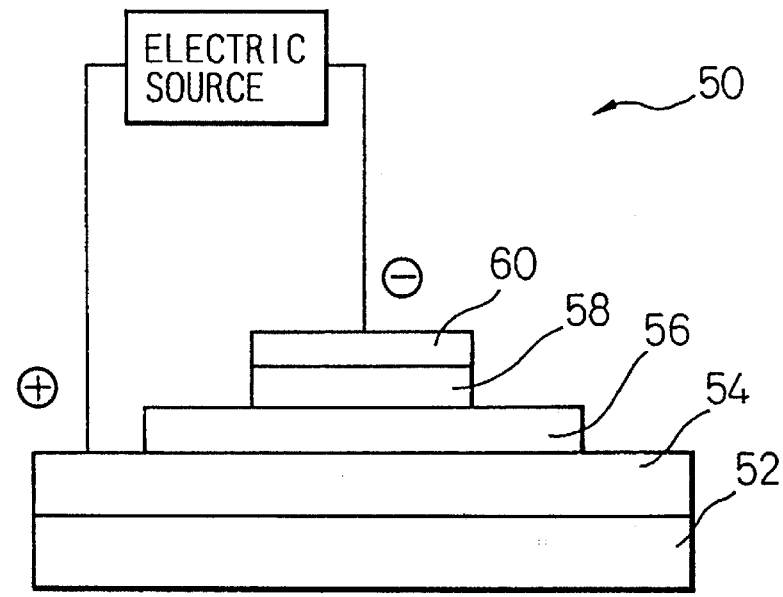
FIG. 2 is a drawing for explanation of another embodiment of an EL device according to the present invention.

The EL device of the present invention may also have the construction shown in FIG. 2. The EL device 50 shown in FIG. 2 comprises an ITO transparent electrode (anode) 54 (indium/tin alloy) formed on a transparent glass plate 52, on which are formed in order a hole injection layer 56 composed of a polycarbonate or other resin, a luminescent layer 58 composed of the 10-hydroxybenzo[h]quinoline zinc complex represented by formula (I), and an upper electrode (cathode) 60 composed of a metal such as aluminum.

Here, the hole injection layer 56 may be formed by dissolution of a polycarbonate or other resin in a solvent such as chloroform, followed by dip coating or spin coating, and the luminescent layer 58 and upper electrode 60 may be formed by continuous deposition in a high vacuum of about $10^{-6}$ to $10^{-5}$ Torr without interrupting the vacuum state.

The anode of this EL device 50 is the ITO transparent electrode 54 and the cathode is the upper electrode 60, and upon the application of a direct current or pulse voltage from a electric source, the luminescent layer 58 emits light.

This type of EL device according to the present invention makes it possible to obtain, at low driving voltages, high-intensity yellow-green to yellow luminescence which has not been possible with conventional EL devices. Furthermore, since it is capable of long-term luminescence, it may be suitably used in backlights for OA machines such as computers and for automobile meters and the like. In addition, since it produces luminescent colors which have not been obtainable with the conventional organic materials for EL devices, there are provided more colors for EL devices.

The present invention will now be explained in more detail with reference to the Examples.

EXAMPLE 1

Synthesis of 10-Hydroxybenzo[h]Quinoline Zinc Complex

A solution of 565 mg of zinc acetate in methanol was slowly added at room temperature to a solution of 976 mg of 10-hydroxybenzo[h]quinoline in methanol.

Next, the mixture was stirred for 2 hours at room temperature and then boiled for 4 hours, and after cooling the precipitate was filtered out.

The filtered precipitate was dispersed in the methanol while being boiled for one hour, and the insoluble portion was filtered out and then washed with hexane and vacuum dried.

Figure 3:
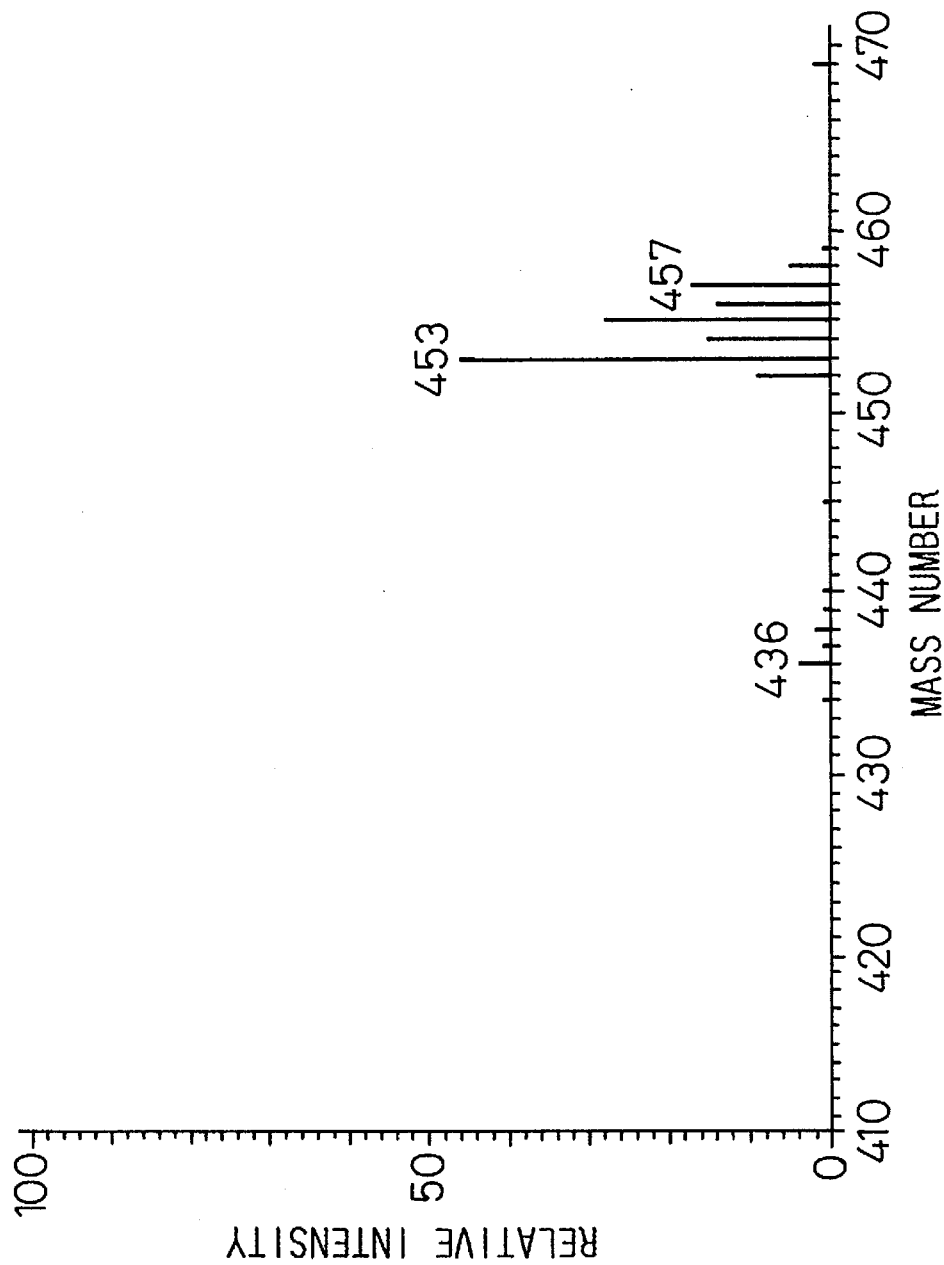
FIG. 3 is a mass spectrogram of the zinc complex of formula (I) used in the present invention.

The yield was 260 mg (22%). Also, upon measurement of the mass spectrum of the zinc complex, the mass spectrogram shown in FIG. 3 was obtained. As shown in FIG. 3, a main peak was observed in the vicinity of a mass number of 453 which is a spectrum specific to the 10-hydroxybenzo[h]quinoline zinc complex.

Preparation of EL Device

The EL device 10 shown in FIG. 1 was prepared by forming in order, on an ITO transparent electrode 14 (indium/tin alloy) having a thickness of about 200 nm formed on a transparent glass plate 12, a hole injection layer 16 having a thickness of about 100 nm and composed of N,N'-diphenyl-N,N'-bis(3-methylphenyl)-[1,1'-biphenyl]-4,4'-diamine, a luminescent layer 18 having a thickness of about 100 nm and composed of the 10-hydroxybenzo[h]quinoline zinc complex synthesized earlier, and an upper electrode 20 having a thickness of about 100 nm and composed of a metal such as aluminum.

The hole injection layer 16, luminescent layer 18 and upper electrode 20 were each formed by vacuum deposition. Specifically, the hole injection layer 16 and luminescent layer 18 were both formed by continuous deposition in a high vacuum of about $10^{-6}$ Torr without interrupting the vacuum state. Consequently, the surface areas of the hole injection layer 16 and the luminescent layer 18 were equal.

Luminescence test

The anode of the EL device 10 shown in FIG. 1 is the ITO transparent electrode 14 and the cathode is the upper electrode 20, and upon the application of a direct current or pulse voltage of 18 V from an electric source, yellow light of an intensity exceeding 1000 cd/m$^2$ was emitted from the luminescent layer 18.

In addition, during the continuous luminescence test the emission of yellow light was stable and continued for over a few hundred hours.

EXAMPLE 2

A luminescence test was conducted in the same manner as in Example 1, except that instead of the EL device 10 of Example 1 having the construction shown in FIG. 1, there was used the EL device 50 having the construction shown in FIG. 2.

The EL device 50 with the construction shown in FIG. 2 was prepared by forming in order, on an ITO transparent electrode 54 (indium/tin alloy) having a thickness of about 200 nm formed on a transparent glass plate 52, a hole injection layer 56 having a thickness of about 100 nm and composed of a polycarbonate resin, a luminescent layer 58 having a thickness of about 100 nm and composed of the 10-hydroxybenzo[h]quinoline zinc complex synthesized in Example 1, and an upper electrode 60 having a thickness of about 100 nm and composed of a metal such as aluminum.

The hole injection layer 56 was formed by dissolution of the polycarbonate resin in chloroform, followed by dip coating or spin coating, and the luminescent layer 58 and upper electrode 60 were formed by continuous deposition in a high vacuum of about $10^{-6}$ to $10^{-5}$ Torr without interrupting the vacuum state. Consequently, the surface areas of the luminescent layer 58 and the upper electrode 60 were equal.

For the luminescence test of the obtained EL device 50, the anode was the ITO transparent electrode 54 and the cathode was the upper electrode 60, and upon the application of a direct current or pulse voltage of 18 V from an electric source, yellow light of an intensity exceeding 1000 cd/m$^2$ was emitted from the luminescent layer 58. In addition, during the continuous luminescence test the emission of yellow light was stable and continued for over a few hundred hours.

We claim:
1. An organic material for EL devices comprising 10-hydroxybenzo[h]quinoline zinc complex represented by the following formula (I):

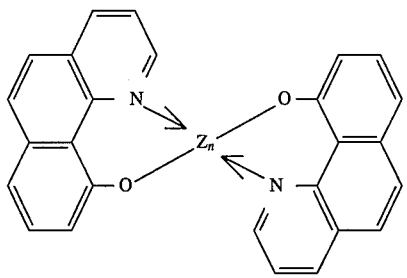
(I)

2. An EL device which comprises in order, an anode layer, a hole injection layer, a luminescent layer and a cathode layer, wherein said luminescent layer comprises 10-hydroxybenzo[h]quinoline zinc complex represented by the following formula (I):

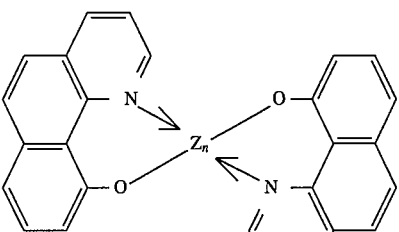
(I)

3. An EL device according to claim 2, wherein said hole injection layer includes a tetraphenyldiamine derivative.

4. An EL device according to claim 2, wherein said hole injection layer includes a polycarbonate resin.

5. An EL device according to claim 2, wherein said anode layer is an ITO transparent electrode.

* * * * *